United States Patent [19]

Percarpio

[11] 4,421,123
[45] Dec. 20, 1983

[54] MULTIPLE SAMPLE NEEDLE VALVE

[75] Inventor: Edward P. Percarpio, North Haledon, N.J.

[73] Assignee: Becton Dickinson and Company, Paramus, N.J.

[21] Appl. No.: 325,704

[22] Filed: Nov. 30, 1981

[51] Int. Cl.³ .............................................. A61B 5/14
[52] U.S. Cl. ................................... 128/766; 128/765; 604/30; 604/256
[58] Field of Search .................. 128/760, 763–768, 128/274, 218 NV; 137/854; 73/864.63–864.67; 604/30, 32–34, 52, 213, 236, 256

[56] References Cited

U.S. PATENT DOCUMENTS

| 274,308 | 3/1883 | George | 137/854 X |
|---|---|---|---|
| 2,128,050 | 8/1938 | Landis | 303/1 |
| 2,663,540 | 12/1953 | Erickson | 251/119 |
| 2,913,000 | 11/1959 | Roberts | 137/854 |
| 3,022,796 | 2/1962 | Cummings | 137/454.6 |
| 3,122,156 | 2/1964 | Kersh | 137/218 |
| 3,331,390 | 7/1967 | Hoffman | 137/854 |
| 3,601,151 | 8/1971 | Winnard | 128/218 NV X |
| 3,817,240 | 6/1974 | Ayres | 128/218 NV X |
| 3,848,579 | 11/1974 | Villa-Real | 128/218 NV X |
| 3,905,386 | 9/1975 | Rachoki | 137/215 |
| 3,949,780 | 4/1976 | Buckman | 137/854 |
| 4,057,050 | 11/1977 | Sarstedt | 128/765 |
| 4,106,497 | 8/1978 | Percarpio | 128/766 |
| 4,200,097 | 4/1980 | Hobbs, Jr. et al. | 128/274 X |
| 4,207,870 | 6/1980 | Eldridge | 128/764 X |
| 4,307,731 | 12/1981 | Kaufman | 128/764 X |

FOREIGN PATENT DOCUMENTS

| 826926 | 1/1952 | Fed. Rep. of Germany . |
| 564936 | 7/1957 | Italy . |
| 1199498 | 7/1970 | United Kingdom . |

Primary Examiner—Lee S. Cohen
Assistant Examiner—Angela D. Sykes
Attorney, Agent, or Firm—Robert P. Grindle

[57] ABSTRACT

A one-way valve is provided for a multiple blood sample needle which valve is self-sealing between the taking of each sample. The valve is a cup valve which utilizes an annular spike arrangement adjacent the bottom of the skirt of the valve for enhancing the sealing effects thereof. In addition, the pedestal-like internal support for the valve is configured to reduce the degree of deflection inwardly of the skirt of the valve, upon opening, which reduction has the effect of reducing the degree of convolution of the circumferential extent of the skirt during the deflection. The revised internal pedestal support reduces, also, any tendency of the valve to cock out of alignment with the longitudinal axis of the valve and its internal support in its normal position.

11 Claims, 3 Drawing Figures

MULTIPLE SAMPLE NEEDLE VALVE

BACKGROUND AND STATEMENT OF THE INVENTION

The subject matter of the invention described and claimed herein is related to the subject matter of U.S. patent application Ser. No. 915,669, filed June 15, 1978, now abandoned, and co-pending U.S. patent application Ser. No. 107,738 filed Dec. 27, 1979, now U.S. Pat. No. 4,307,731, issued Dec. 29, 1981 which applications are hereby incorporated by reference in their entirety.

Generally speaking, this invention relates to blood sampling devices. More particularly, this invention relates to such devices for taking multiple sample collections. Many different forms of valve assemblies have been designed in the past for controlling the direction of flow of fluids. These include, for example, ball and seat valves, duck bill valves, and cup-shaped or conical valves. It is the latter form of valve to which this invention is directed and such valves operate by compressing or folding their elastomeric skirts under sufficient pressure for permitting fluids to pass by around the skirt. Flow of fluid in the opposite direction, toward the center of the skirt has the effect of expanding the flexible skirt portion into sealing contact with the adjacent cooperating walls in the chamber where the skirt valve is fixed. U.S. Pat. No. 2,913,000, for example, discloses a cup-shaped flow control valve which operates in this manner.

While such cup valves have proved useful in multiple blood sampling assemblies, enabling the user to exchange evacuated blood collection tubes without undo leakage due to venous or tourniquet pressure, and while such assemblies have provided simple, inexpensive arrangements, they have not been entirely satisfactory in that the degree of leakage has been somewhat too high in some applications, and the support arrangement for the cup valve has not been substantial enough and configured in a manner whereby prevention of cocking of the valve is completely achieved.

With this invention, by contrast, a cup valve arrangement is provided which has the effect of reducing substantially to zero any leakage around the circumferential bottom edge of the skirt of the cup valve and, simultaneously, reducing the cocking of the valve from its normal position to acceptable limits. This is achieved by incorporating an annular spike or sealing ring adjacent the bottom edge of the skirt of the valve for enhancing the sealing effect between the valve skirt and the adjacent cooperating valve chamber walls. In addition, the internal pedestal support for the valve has been enlarged and reconfigured to provide a more substantial support for the cup valve, for reducing any cocking thereof.

It is, therefore, among the primary objects of the invention to provide a blood sampling assembly with a valve member having a resilient skirt which has both a multiple sampling feature and the capability of acting as a check valve.

It is a further object of the invention to provide a valve member with means which reduces to a minimum any cocking of the valve from its normal position. A still further object of the invention is to provide a cup-shaped check valve which operates to reduce substantially to zero any leakage around the valve in its closed position. A further object of the invention is to provide a cup-shaped check valve and a blood sampling assembly therefore which may be mass produced in economical fashion.

The valve assembly, in accordance herewith, has a resilient skirt which will collapse under sufficient pressure in one direction of flow, and which will expand against the walls of a fluid conduit or chamber in which it is positioned to prevent flow in the opposite direction. Positioned centrally of the cup valve along the axis thereof is a protrusion which serves to cooperate with the pedestal support therefore to provide the support for the cup valve, in accordance herewith, in its various positions of operation.

Before describing this invention in more detail, it may be well to note that the cup valve of the invention may be comprised of any conventional elastomer, such as natural or synthetic rubber. Satisfactory results have been achieved, in accordance herewith, with a natural rubber formulation number VL601M105 manufactured by Vernay Laboratories, Inc., Yellow Springs, Ohio.

An advantage of the invention herein, as applied to multiple sampling needles, is that the one-way cup-valve prevents chemical additives within an evacuated container attached to the assembly, in accordance herewith, from entering the bloodstream. If a tourniquet is removed or loosened before the intravenous needle is withdrawn from the vein, a reverse pressure could cause backflow. With the improved structure, in accordance herewith, such a risk is eliminated. That is, the circumferential spike together with the bottom of the skirt of the cup valve in accordance herewith, when viewed in section, is in the form of a ring under compression. Any deflection thereof inwardly, causes convolution of that ring. By incorporating the spike, in accordance herewith, the degree of convolution is reduced, thus eliminating leakage between the cooperating surfaces of the cup valve and its adjacent chamber walls in the sealing position thereof. In addition, the invention herein includes a substantially larger and differently configured pedestal centrally of the cup valve which serves as the support for the cup valve. This larger negative pressure hub pedestal has the effect of maintaining the valve "squared". That is, the axis of the cup-shaped valve is maintained adjacent the axis of the pedestal support which supports it.

Other objects and advantages of this invention will be apparent from the following description, the accompanying drawings and the appended claims.

DETAILED DESCRIPTION OF THE INVENTION

Figure 1:
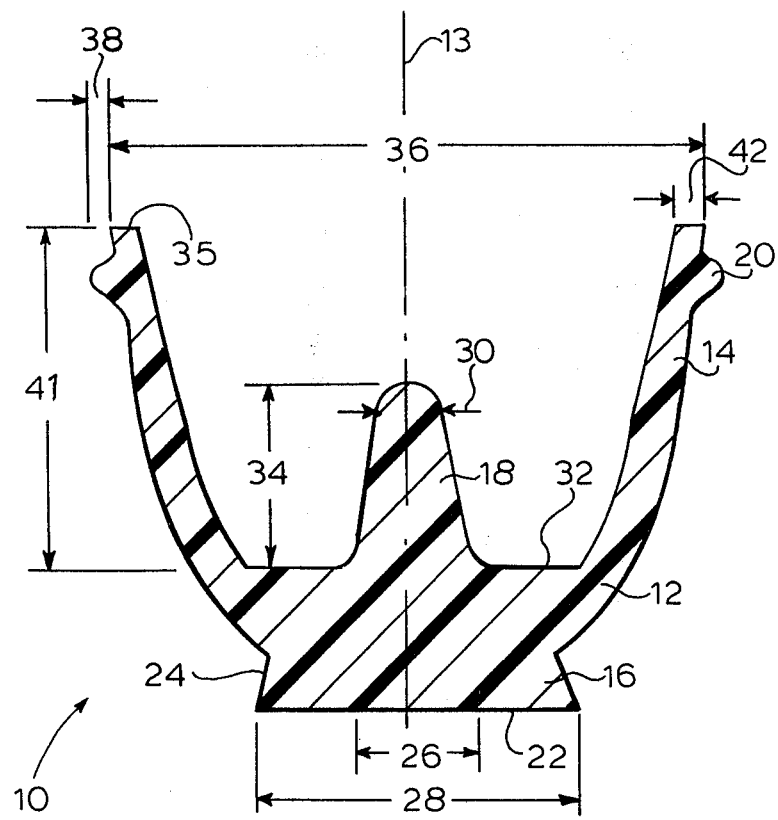
FIG. 1 is a cross-sectional view of a cup-shaped valve illustrating the invention.

Referring to the drawings in which like reference characters refer to like parts throughout the several views thereof, FIG. 1 illustrates the cup-shaped valve 10 of the invention in section having a body portion 12 with an integral annular skirt 14. The skirt 14 flares outwardly from the body portion 12 at about 7° from the longitudinal axis 13 of the valve. The annular skirt 14, defines the cup-shaped valve portion of the valve, in accordance herewith. An integral protrusion 18 extends from body portion 12 along axis 13 of the valve. The protrusion 18 serves to support the valve when mounted in the assembly, as discussed below. Surrounding the protrusion 18 is an annular flat surface 32 which also serves to cooperate with the pedestal support for the valve in its assembled position, as discussed below.

As is shown in FIG. 1, the protrusion 18 is relatively thick at its point of attachment to the body portion 12 and tapers to a rounded end. Adjacent the lower end 35 of skirt 14, and spaced therefrom is an annular spike 20 extending outwardly from the skirt 14. This spike, in the assembled position of the valve, has the effect of enhancing the sealing engagement of the valve with the adjacent cooperating walls of the assembly, in accordance herewith.

On the side of valve body 12 opposite the skirt, the valve member includes a flattened annular projection 16 which is positioned equi-laterally of the axis 13 of the valve of the invention, and includes a flat surface 22 which is connected to body portion 12 by a tapered wall 24. The taper may be, for example, about 20° relative to axis 13.

As will be appreciated, the dimensions of the valve, in accordance herewith, as shown in FIG. 1 may vary, according to the size of the assembly prepared for use. However, as illustrative of dimensions which may be utilized in a conventional multiple blood sampling assembly, the diameter 36 of the valve, as illustrated in FIG. 1 may be, for example, 0.194 inches plus or minus 0.003 inches. With that size valve diameter, dimension 38 of the annular spike 20 extending from the outer wall of skirt 14 is 0.005 inches. It should be understood, further that in molding the valve 10, the sealing surface of spike 20 must be continuous without any imperfection, in order to reduce to zero any leaks in the assembled position of the valve 10.

Given the above valve 10 dimensions, the length 34 of pedestal 18 is 0.06 inches, and the dimension 41 as shown in FIG. 1 is 0.11 inches. The width 42 of the bottom edge 35 of skirt 14 is 0.008 inches. The dimension 30 adjacent the end of pedestal 18 is 0.065 inches. The width 28 of flat surface 22 of the valve 10 is 0.108 inches, while the width 26 of pedestal 18 where it joins body portion 12 is 0.04 inches. It is important in molding the valve, in accordance herewith, that no trim or flash is left to extend from the end surface 35 of skirt 14, because this has an effect on the sealing engagement properties of the valve, in its assembled position.

Figure 2:
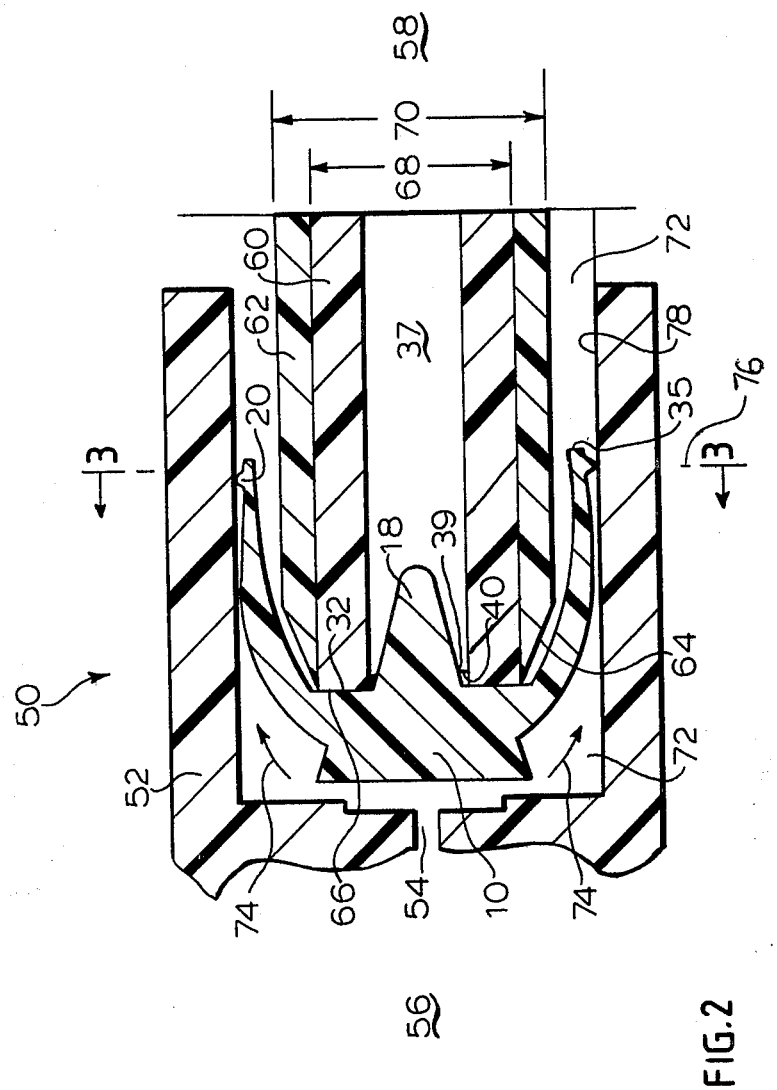
FIG. 2 is a partial longitudinal sectional view of a multiple sample blood collection assembly illustrating the invention, and incorporating the cup-shaped valve of FIG. 1.

Referring now to FIG. 2, a partial assembly of a multiple blood sampling arrangement, in accordance herewith, is shown with the assembly 50 having cooperating portions 52 from the I.V. end 56 of the assembly cooperating with the support pedestal 60, 62 of the negative pressure end 58 of the assembly. In this connection, reference is made to U.S. application Ser. No. 107,738, referred to above, for details of the remaining portions of a blood sampling assembly, in accordance herewith, including the I.V. cannula mounting arrangement which is in flow communication with passage 54 for receiving and directing intravenous blood to chamber 72 in the direction of arrows 74. The supporting pedestal 60, 62, in accordance herewith, extends from the negative pressure hub, as described in the co-pending application referred to above, and mounts a negative pressure cannula and a holder for receiving an evacuated tube, none of which parts are shown since they are conventional and are familiar to practitioners-in-the-art.

Figure 3:
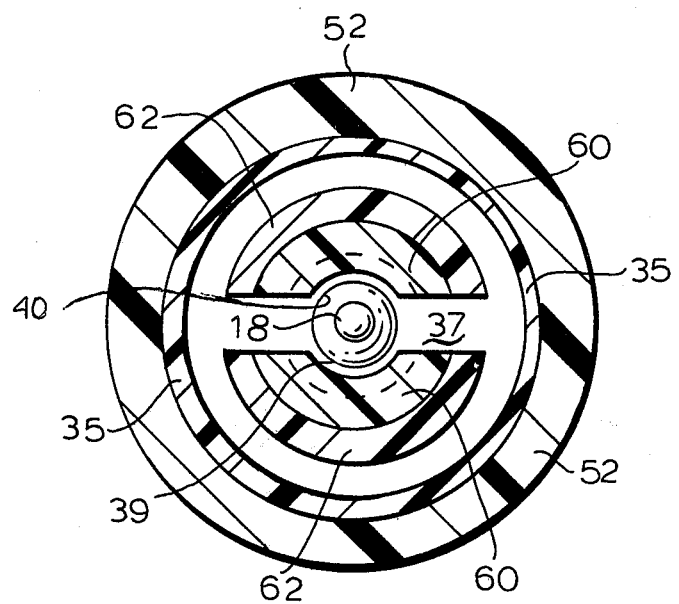
FIG. 3 is a sectional view taken along lines III—III of FIG. 2.

As can be seen in FIG. 2, the cup-shaped valve 10 of the invention is mounted on a support pedestal-like assembly 60, 62 with the pedestal support, in the part shown in FIG. 2 being in the form of two halves, as illustrated in FIG. 3 with a central opening 37 for receiving the protrusion 18. As can be seen, the annular flat surface 32 of valve body 12 cooperates with the annular flat surface 66 at the top of the pedestal support 60,62, as do the cooperating annular edges 39, 40.

As a further important feature of this invention, the pedestal support 60 includes the additional annular dimension 62 which has a tapered upper surface 64 converging in the I.V. direction toward the longitudinal axis of the assembly. This additional support, in the configuration shown, serves to provide a more uniform support for the cup-shaped valve 10 in its mounted position. Thus, the cooperating flat surfaces together with the cooperating taper 64 serve to limit the convolution of the lower edge 35 of the skirt portion 14 of the cup-shaped valve. The movement of the lower end of the skirt, in other words, the lip motion of the skirt lower edge 35 is reduced to 0.01 inches of movement from a closed to an open position, and vice versa, because of the combination of the newly configured pedestal support 60, 62, in accordance herewith, together with the action of the sealing spike 20. This limited motion of the lower end of the skirt, into and out of sealing engagement with the internal surface 78 of chamber 72 in which the valve assembly 10 is mounted reduces, as discussed above, the degree of convolution of the "ring" which is the lower end of the skirt. By reducing the degree of convolution, as will be appreciated, the valve cooperates with the internal surface 78 to provide proper sealing engagement.

In addition, because of the increased more stable support of the internal pedestal 60, 62, and its particular configuration relative to the cup-shaped valve 10, the valve 10 is not cocked out of alignment with the longitudinal axis of the assembly, shown in FIG. 2, more than 0.035 inches in the longitudinal direction of the assembly. That is, the lower annular end 35 of the cup-shaped valve assembly 10 does not move on either side of the longitudinal axis of the assembly shown in FIG. 2 longitudinally in either direction of the section line 76 more than 0.035 inches from the squared position as shown in FIG. 2.

With respect to the increased size of the support pedestal 60, 62, in accordance with this invention, the dimension 68 of the prior art centrally arranged support was 0.10 inches, while the dimension 70, which is the diameter of the support relative to the dimensions described previously for a representative cup valve 10, as discussed above, is 0.134 inches. As will be appreciated, the diameter of the support pedestal has been increased substantially one-third and together with the taper 64 provides the "squared" support required for the valve assembly 10 to prevent the cocking thereof out of longitudinal alignment, as discussed above.

In operation, the multiple blood sampling assembly, in accordance herewith operates in much the same manner as the assembly shown and described in U.S. patent application Ser. No. 107,738. That is, a holder is mounted on the negative pressure hub of the assembly. Thereafter, an intravenous cannula is made to penetrate a vein and blood flows through the cannula, then through passage 54 and into chamber 72. During this period of time, as will be appreciated, the cup-shaped valve 10, in accordance herewith, is in the position shown in FIG. 2 with the spike 20 in sealing engagement with the internal walls 78 of chamber 72. The valve member 20 is constructed, as will be appreciated, so that blood does not pass therethrough under venous pressure, even if a tourniquet has been utilized.

Once a vein is found to be punctured, an evacuated tube having a resilient stopper may be inserted at the negative pressure end of the assembly within the previously attached holder, in conventional manner. Once the evacuated tube stopper is pierced by the negative pressure cannula, under the large pressure differential the skirt 14 of valve 10 deflects inwardly adjacent the annular lower end 35 thereof to allow the flow of blood past annular spike 20 and into the evacuated tube. Once filled, the tube is removed from the holder at which time the skirt of the cup-shaped valve expands against the chamber walls 78 to prevent any reverse flow and contamination of a patient. It will be appreciated that, subsequently, a series of evacuated tubes may be connected to the assembly for a multiple sample taking of the blood.

Thus, as will be appreciated from the above discussion, a one-way valve is provided in accordance herewith for a multiple blood sample needle assembly which valve operates to be self-sealing between the taking of each sample. Moreover, a multiple blood sample assembly is provided which includes an improved support pedestal for cooperation with the one-way valve, in accordance with this invention, to provide a much improved operating assembly for the taking of multiple blood samples. The arrangement is such that the possibility of the cup valve cocking out of alignment in a manner which would effectively negate the operating efficiency of the assembly, is eliminated, together with any leakage past the valve, in its closed position.

While the forms of apparatus herein described constitute preferred embodiments of the invention, it is to be understood that the invention is not limited to these precise forms of apparatus, and that changes may be made therein without departing from the scope of the invention which is defined in the appended claims.

What is claimed is:

1. A cup valve apparatus for a multiple blood sample assembly, comprising
   (a) an annular valve body;
   (b) an annular valve skirt having an upper and lower end, said valve skirt depending from said valve body at the upper end of said skirt and integral therewith, said skirt diverging from the axis of said body;
   (c) an integral support protrusion extending from said valve body centrally of said skirt along the axis of said body;
   (d) a flattened annular projection extending from said body on the side thereof opposite said skirt and said protrusion, said projection being coaxial with said body;
   the improvement characterized by
   (e) an integral annular spike on said skirt adjacent the lower end thereof; and
   (f) said spike extending radially from the side wall of said skirt.

2. The apparatus of claim 1, further characterized by
   (a) said skirt diverging from the axis of said body substantially seven degrees.

3. The apparatus of claim 1, further characterized by
   (a) said valve body and valve skirt are natural rubber.

4. The apparatus of claim 1, further characterized by
   (a) the diameter of said skirt adjacent the lower end thereof is within the range of between about 0.191 and 0.197 inches; and
   (b) the width of said annular spike is 0.005 inches.

5. A multiple sample blood collection apparatus comprising
   (a) a housing having a chamber disposed therein;
   (b) said chamber having an intravenous end adapted to be in flow communication with a blood source, and a negative pressure end adapted to be in flow communication with a negative pressure source;
   (c) an annular valve body disposed in said chamber;
   (d) an annular valve skirt having an upper and lower end, said valve skirt depending from said valve body at the upper end of said skirt and integral therewith; said skirt diverging from the axis of said valve body toward said negative pressure end; said chamber having walls adjacent said valve skirt;
   (e) an integral support protrusion extending from said valve body centrally of said skirt along the axis of said body;
   (f) a flattened annular projection extending from said body on the side thereof opposite said skirt and said protrusion, said projection being coaxial with said body;
   (g) a coaxial valve mounting structure positioned centrally in said chamber and extending from the negative pressure end thereof;
   (h) a recess in said valve mounting structure receiving said support protrusion on said valve;
   the improvement characterized by
   (i) an integral annular spike on said skirt adjacent the lower end thereof; and
   (j) said spike extending radially from the side wall of said skirt and being in cooperating sealing engagement with the walls of said housing chamber adjacent said spike.

6. The apparatus of claim 5, further characterized by
   (a) said skirt diverging from the axis of said body substantially seven degrees in its unmounted position.

7. The apparatus of claim 5, further characterized by
   (a) said valve body and valve skirt are natural rubber.

8. The apparatus of claim 5, further characterized by
   (a) the diameter of said skirt adjacent the lower end thereof is within the range of between about 0.191 and 0.197 inches prior to insertion into said chamber; and
   (b) the width of said annular spike is 0.005 inches.

9. The apparatus of claim 8, further characterized by
   (a) said valve body has an annular flat surface surrounding said support protrusion;
   (b) said valve mounting structure having a flat top engaging surface engaging said flattened annular projection of said valve body;
   (c) said valve mounting structure being cylindrical at said flat top engaging surface;
   (d) said recess of said valve mounting structure being a slotted hole defining two semi-cylindrical portions,
   (e) an integral enlarged annular portion on said valve mounting structure, said enlarged portion having a top surface, the top surface of said enlarged portion diverging from said flat top engaging surface toward the negative pressure end of said chamber.

10. The apparatus of claim 9, further characterized by (a) the diameter of said valve mounting structure is 0.10 inches; and
(b) the diameter of said integral enlarged annular portion is 0.134 inches.

11. The apparatus of claim 10, further characterized by
(a) said spike on said valve skirt and said enlarged annular portion on said valve mounting structure cooperating to limit the movement of said valve skirt from an opened position thereof away from said adjacent chamber walls to a closed position thereof against said adjacent chamber walls, and vice versa.

* * * * *